(12) United States Patent
Bernkop-Schnürch (10) Patent No.: US 7,354,600 B1
(45) Date of Patent: Apr. 8, 2008

(54) MUCO-ADHESIVE POLYMERS, USE THEREOF AND METHOD FOR PRODUCING THE SAME

(76) Inventor: Andreas Bernkop-Schnürch, Christophgasse 6/11, A-1050, Vienna (AT)

( * ) Notice: Subject to any disclaimer, the term of this patent is extended or adjusted under 35 U.S.C. 154(b) by 0 days.

(21) Appl. No.: 09/830,986

(22) PCT Filed: Nov. 4, 1999

(86) PCT No.: PCT/AT99/00265

§ 371 (c)(1),
(2), (4) Date: May 3, 2001

(87) PCT Pub. No.: WO00/25823

PCT Pub. Date: May 11, 2000

(30) Foreign Application Priority Data

Nov. 4, 1998 (AT) .................................. 1828/98

(51) Int. Cl.
*A61K 9/14* (2006.01)
(52) U.S. Cl. .................................. 424/486; 514/54
(58) Field of Classification Search ............... 424/486, 424/484, 485, 487, 488; 523/118; 530/356; 526/286, 287, 288, 289; 514/54
See application file for complete search history.

(56) References Cited

U.S. PATENT DOCUMENTS

| 5,064,495 A * | 11/1991 | Omura et al. ............ 156/307.3 |
| 5,412,076 A | 5/1995 | Gagnieu |
| 5,496,872 A | 3/1996 | Constancis et al. |
| 5,646,239 A | 7/1997 | Constancis et al. |
| 5,665,383 A | 9/1997 | Grinstaff et al. |
| 5,670,468 A * | 9/1997 | Moens ..................... 510/220 |
| 6,514,535 B2 * | 2/2003 | Marchant ................. 424/486 |

FOREIGN PATENT DOCUMENTS

| EP | 0 556 110 | 8/1993 |
| EP | 0 635 276 | 1/1995 |
| WO | 94/13731 | 6/1994 |
| WO | 96/06880 | 3/1996 |

OTHER PUBLICATIONS

Bernkop-Schnurch et al, "Development and in vitro evaluation of a drug delivery system protecting from trypsinic degradation," International Journal of Pharmaceutics, vol. 157, 1997, pp. 17-25.*
Bernkop-Schnurch et al, "Synthesis and evaluation of a modified mucoadhesive polymer protecting from alpha-chymotrypsin degradation," International Journal of Pharmaceutics, vol. 146, 1997, pp. 247-254.*
Bernkop-Schnurch et al (Pharmaceutical Research, vol. 16, No. 6, 1999).*
H.L. Lueβen et al, "Mucoadhesive polymers in peroral peptide drug delivery. IV. Polycarbophil and chitosan are potent enhancers of peptide transport across intestinal mucosae in vitro" Journal of Controlled Release 45 (1997) 15-23.
Michael J. Tobyn et al, "Factors Affecting in vitro Gastric Mucoadhesion II. Physical Properties of Polymers" European Journal of Pharmaceutics and Biopharmaceutics 42, Jan. 1, 1996.

* cited by examiner

*Primary Examiner*—Sreeni Padmanabhan
*Assistant Examiner*—Umamaheswari Ramachandran
(74) *Attorney, Agent, or Firm*—Buchanan Ingersoll & Rooney PC (57) ABSTRACT

Mucoadhesive polymers, the use thereof and a production method therefor. Mucoadhesive polymers assembled of not more than 10 different monomers and comprising at least one non-terminal thiol group, as well as drugs containing these polymers are described.

35 Claims, 7 Drawing Sheets

FIG. 6 though only a weak bond is
MUCO-ADHESIVE POLYMERS, USE THEREOF AND METHOD FOR PRODUCING THE SAME The invention relates to mucoadhesive polymers, drugs comprising such polymers as well as the use of mucoadhesive polymers.

Since the introduction of the concept of bioadhesion in the pharmaceutical literature, many attempts have been made in university and industrial fields to improve the bioadhesive properties of various polymers. These attempts included the neutralization of ionogenic polymers (Tobyn et al., Eur. J. Pharm. Biopharm. 42 (1996) 56-61), the precipitation of polymers in organic solvents, and their drying in air instead of lyophilization (Bernkop-Schnürch et al., Int. J. Pharm. 165 (1998) 217-225), the development of polymer-lectin conjugates (Naisbett et al., Int. J. Pharm. 107 (1994) 223-230) as well as conjugates of polymers and bacterial adhesin (Bernkop-Schnürch et al., J. Pharm. Sci. 3 (1995) 293-299).

These systems which have been described are all based on the formation of non-covalent bonds, such as, e.g., hydrogen bonds or ionic interactions, with which only a weak bond is enabled which in many cases is insufficient for a satisfactory localization of the active substance-delivery system at a certain target site.

That mucus layer which coats GI epithelia mainly consists of mucus glycoproteins which comprise a central region with numerous O-linked oligosaccharide chains and two flanking cysteine-rich subdomains on either side. These cysteine-rich subdomains contain more than 10% Cys in their primary structures which are involved when mucin monomers are linked to give oligomers via disulfide bonds. In this manner, a three-dimensional network of the mucus gel layer is built up.

The object of the present invention consists in providing improved mucoadhesive polymers which enable a targeted introduction of active substance in mucus layers, wherein a stable presence at the target site shall be enabled. By this invention, an effective and efficient active substance delivery system shall be enabled by which an improved and thus also extended adhesion of drug on the mucosae can be attained.

According to the invention, this object is achieved by a mucoadhesive polymer which is characterized in that it is assembled of not more than 10 different monomers and comprises at least one non-terminal thiol group. By the targeted introduction of thiol groups in polymers known to have mucoadhesive properties or by creating completely new thiol-containing polymers, the specific structure of mucus layers is utilized in a specific manner: It has been known that the mucolytic activity of thiols, such as, e.g., N-acetyl cysteine, is based on disulfide exchange reactions between glycoproteins in the mucus and the mucolytically active agent. Based on such exchange reactions, both intra- and also inter-molecular disulfide bonds in the glycoprotein structure of the mucus are cleaved, thereby dissolving the mucus layer. Based on this observation, according to which a mucolytic substance is covalently bound to glycoproteins in mucus, according to the invention the hypothesis was set up that other thiol-containing compounds, in particular polymers with thiol-groups, also could covalently be bound to a mucus layer. Surprisingly, it has been found that this hypothesis not only is completely accurate, but also acts so specifically that it provides an efficient drug delivery system. In particular, it has been shown that in contrast to mucolytic thiols, the polymers according to the invention do not have any substantial mucolytic activity.

Figure 1:
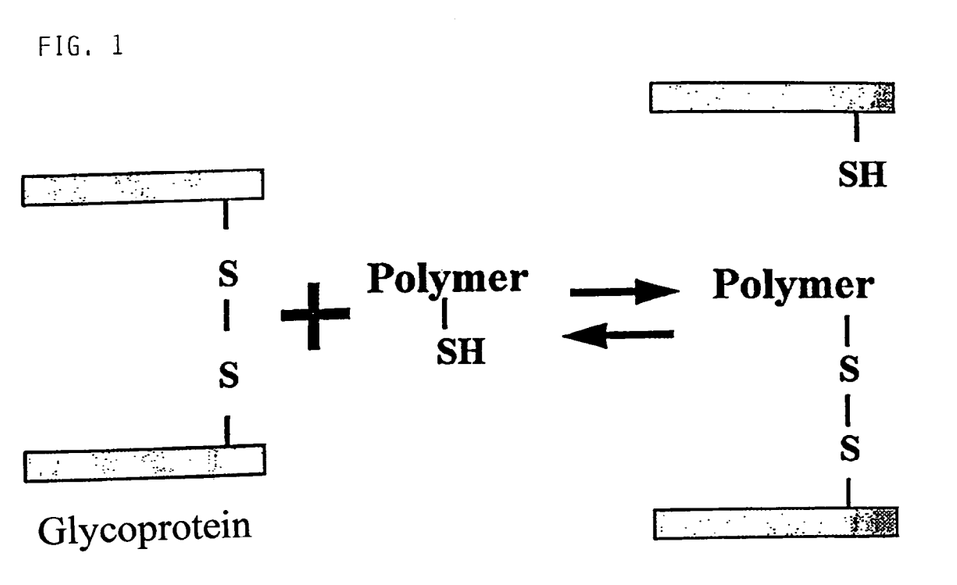
FIG. 1 shows the principle of the covalent binding of the polymers of the invention to the mucus layer.

It has been shown that the polymers according to the invention are capable of forming reversible, covalent bonds with the cysteine-rich subdomains of the mucus glycoproteins (cf. FIG. 1), such bonds allowing for a stable localization of the polymers on certain mucosae in the mucus.

Preferably, the polymers according to the invention comprise at least 0.05 mmol, in particular at least 0.1 µmol, covalently bound thiol groups per gram of polymer. Usually, the polymers according to the invention comprise 1-500 µmol thiol groups per gram of polymer, in particular 10-100 µmol. This not only allows for an efficient binding to the mucus glycoproteins, but also enhances their mucoadhesive properties due to advantageous hydration effects and internal cohesion.

Preferably, the polymers according to the invention are prepared by thiolation of polymers which have already been known to have mucoadhesive properties. In doing so, such mucoadhesive property substantially is enhanced and improved. Therefore, the polymer of the invention preferably is selected from a thiolated polycarbophil (a copolymer of acrylic acid and divinyl glycol), thiolated chitosan, thiolated sodium carboxymethylcellulose, thiolated sodium alginate, thiolated sodium hydroxypropylcellulose, thiolated hyaluronic acid and thiolated pectin. For the non-thiolated base polymers, the mucoadhesive property has, e.g., been described in Smart et al. (J. Pharm. Pharmacol. 36 (1984) 295-299).

Of course, also the thiolated derivatives of the above-mentioned polymers are preferred. Examples of such derivatives comprise derivatives obtained by auto-cross-linking, introduction of functional groups, attachment of complexing agents (such as, e.g., EDTA), coupling of enzyme inhibitors, etc., in particular in case of polymers comprising negatively charged groups, e.g. $COO^-$ groups.

According to the invention, such thiolation may be effected by all types of chemical reactions, by which thiol groups are bound to polymers, in particular to water-soluble polymers. For economical reasons, the use of cysteine groups lends itself for thiolation because the latter are easy and inexpensive to obtain. Cysteine groups may preferably be bound to the polymer via an amide bond.

On the other hand, the polymer according to the invention may also be prepared in that in the course of producing said polymer, at least one monomer is (co)-polymerized with thiol groups, which monomer comprises free thiol groups in the polymer, i.e. the thiol group is not directly reacted in the polymerization reaction. Such a polymer which comprises at least one monomer that has free thiol groups in the polymer is also preferred according to the invention.

Preferred polymers according to the invention are also characterized by a high binding capacity to intestinal mucosa which, measured as total work of adhesion (TWA) is higher than 120 µJ, in particular higher than 150 µJ (at pH 7). A system suitable for measuring such TWA will be described in the examples.

According to the invention, preferably polymers are used which, compared to the TWA of the non-thiolated polymer, have an increased TWA. Preferably, this increase in TWA is 50% or more, in particular 100% or more, measured at the pH optimum of the TWA of the thiolated polymer.

In a further aspect the present invention relates to a drug comprising a polymer according to the invention and at least one active substance which is taken up via the mucosae. Since a targeted application of active substances on mucus layers is possible with the polymers of the invention, the drug according to the invention is superior to all previously known systems of delivering an active substance to mucus layers, both as regards its specificity and as regards its general applicability.

Preferably, the active substance is non-covalently bound to the polymer, thus enabling an administration of the active substance at the target site by diffusion. The manner in which the active substance and the polymer are intermingled or interlinked is not critical, co-lyophilization i.a. being just as usable as air drying, gelling etc. Also the manner in which the drug is finally confectioned is not critical, preferably, however, it is provided as a tablet, suppository, pellet, eye, nose, ear drops or gels, in a form to be administered by inhaling or in the form of micro(nano) particles.

As the active substances, preferably substances will be considered which are known to have an activity on the mucus layer, in particular those substances which have a comparatively short elimination half life in blood, e.g. less than 3 hours. On account of an improved and extended adhesion of the active substance in the active substance delivery systems based on the thiolated polymers of the invention, which systems, moreover, allow for a controlled release of the active substance over several hours, the frequency of ingestion for such active substances can be reduced dramatically.

According to a preferred embodiment, the drug of the invention contains active substances which are enhanced by thiol groups, preferably thiol-dependent enzymes, in particular papain and subtilisin.

In a further aspect the present invention relates to the polymer of the invention as a drug and to the use of a polymer of the invention for preparing a drug, in particular a mucoadhesive drug. Preferably, this drug can be administered perorally.

The inventive form of administration also allows for a delayed release of the active substance, e.g. by providing the active substance within a polymer tablet, wherein the delay is effected by the active substance having to penetrate through the polymer coat. In this respect, particularly the improved swelling behavior of the polymers of the invention caused by the thiol groups plays an important role.

According to the invention, administration of the drug to patients is effected in an efficient dose, wherein the dose may be in line with dosages described in the prior art for the respective active substance. In this respect, however, two aspects need to be taken into consideration: on the one hand, the form of administration according to the invention is quite more targeted and more efficient than the known administration (by the same route of administration), and on the other hand, the permeation of active substances through the mucosa can be enhanced by the polymers of the invention.

Accordingly, a preferred embodiment of the present invention relates to the use of the polymer of the invention for preparing an agent for enhancing the permeation of active substances, in particular of high-molecular, hydrophilic substances, e.g. active (poly) peptide substances, through a mucosa, preferably through the intestinal mucosa.

It has been shown that the polymers according to the invention are also capable of binding certain ions, in particular zinc ions. By administering the polymer of the invention, zinc ions of the polymer will be bound at the site of adhesion, whereby enzymes, in particular enzymes dependent on zinc ions, are inhibited. An inhibition of enzymes may also be effected by the enzymes directly binding to the polymer according to the invention. The present invention thus also relates to the use of the polymer according to the invention for preparing an agent for inhibiting enzymes, in particular enzymes dependent on zinc-ions. Examples thereof are particularly zinc-dependent enzymes in the gastro-intestinal tract, such as carboxy peptidases A and B.

In a further aspect, the present invention also relates to the use of the polymers according to the invention at non-mucous contact layers, with the improved adhesion properties to biological (proteinaceous) material also being utilized. In particular, applications in visco-surgery (intraocular surgical interventions, cataract treatment), intradermal applications (cosmetic, yet also therapeutical ones; e.g. the smoothing of wrinkles, or tissue augmentation), yet also intraarticular, in particular synovial, applications are under consideration.

As mentioned above, the preparation of the polymers of the invention is not critical; a preferred method of preparing the polymers according to the invention is characterized in that base polymers assembled of not more than 10 different monomers, wherein at least one of the non-terminal monomers comprises a terminal, functional group I that is free within the polymer, are reacted with thiol-containing compounds comprising at least one further functional group II, the functional groups I and II forming a covalent bond with each other during this reaction, optionally with the use of coupling reagents.

Preferably, functional group I in this method is a carboxyl group, and functional group II is an amino group, preferably a primary amino group, an amide bond being formed. Coupling reagents, in particular carbodiimides, may preferably be used in the reaction.

According to a preferred embodiment, a mercapto compound having a primary amino group, preferably cysteine or a cysteine derivative, is used as the thiol-containing compound.

Preferably, the reaction is carried out at a pH of between 4 and 8, in particular at 5.5 to 6.5.

The polymer prepared according to the invention may be adjusted to a certain pH, preferably to a pH of between 5 and 9, in particular from 6.5 to 8.5.

In a further aspect, the present invention also relates to a method of improving the mucoadhesion of polymers, which method is characterised in that laterally arranged thiol structures are introduced into these polymers, resulting in the formation of disulfide bonds between the polymer and the mucus layer.

The invention will now be described in more detail and with reference to the following examples and the drawing figures, wherein

FIG. 3 shows the release profile of rifampicin from thiolated and non-thiolated CMC (FIG. 3A) and thiolated and non-thiolated PCP (FIG. 3B);

EXAMPLE 1

Preparation of a Polymer According to the Invention 10 g of polycarbophil (Noveon AA1, from BF Goodrich) were suspended in portions in 100 ml of a 4% (m/m) methanolic NaOH solution with continuous stirring. The resultant sodium salt of the polymer is filtered off and washed with methanol until the filtrate has a neutral pH. Subsequently, the polymer is dried at room temperature in the exsiccator. One gram of neutralized polycarbophil is hydrated in 250 ml of demineralized water, and the carboxylic acid groups of the polymer are pre-activated at room temperature for 45 min and under stirring with 1-ethyl-3-(3-dimethylamino propyl)-carbodiimide hydrochloride which is added to a final concentration of 50 mM. To prevent an oxidation of the L-cysteine subsequently added, the pH of the solution is adjusted with 5 N HCl to pH 4 and admitted with $N_2$ gas for 15 minutes. After the addition of 0.5 g of L-cysteine, the pH of the solution optionally is readjusted with HCl or NaOH, respectively, to a pH of 4-5, and the reaction mixture is stirred for 3 h at room temperature and under supply of $N_2$ gas. The polycarbophil-cysteine conjugate is dialyzed against an aqueous 1 mM HCl and 2 μM EDTA solution, twice against the same dialysis medium yet additionally containing 1% NaCl, and subsequently exhaustively against 0.5 mM HCl at 10° C. under the exclusion of air. Thereafter, the pH of the conjugate is adjusted with 1 N NaOH to pH 5. The isolated conjugate is freeze-dried at −30° C. Storage is effected at 4° C.

Various polycarbophil(PCP)-cysteine conjugates were prepared which had the following thiol group concentrations (in μmol/g of polymer): PCP-Cyst 1:4: 142.2±38.0 mmol/g polymer; PCP-Cyst 1:2: 12.4±2.3; PCP-Cyst 2:1: 5.3±2.4; PCP-Cyst 4:1: 3.2±2.0; PCP-Cyst 8:1: 2.9±1.4; PCP-Cyst 16:1: 0.6±0.7; PCP-Cyst 32:1: 0.3±0.5; control: (PCP+Cyst without reaction): 0.00±0.00 (this demonstrated the efficiency of purification).

Especially the PCP-Cyst conjugates 1:2 and 1:4 exhibited a significantly (>100%) higher water uptake capacity as compared to the non-modified polymer.

In mucin binding studies (binding of porcine mucin to the polymers) it could be demonstrated that mucins were effectively bound to the polymer-cysteine conjugate tested (in contrast to the non-modified polymers).

The binding strengths (TWA) of the polymers of the invention to mucins of the intestinal mucosa were tested substantially as in Ch'ng et al. (J. Pharm. Sci. 74 (1985) 399-405), carried out as described in Bernkop-Schnürch et al. (Pharm. Res. 16(6) (1999), 876-881)

Both in adhesion tests and in ex-vivo studies on mucosa excized porcine small intestines in synthetic intestinal fluid consisting of 50 mM-Tris-HCl buffer, pH 6.8, containing 0.9% NaCl, the polymer(polycarbophil)-cysteine conjugate described here exhibited a clearly higher adhesive capability than polycarbophil pre-treated in the same manner, to which, however, no cysteine had covalently been bound.

It could be demonstrated that with the polymers according to the invention, the adhesive action relative to non-modified polymer (PCP) could be increased by at least 100%. Thus, e.g., with the polymer-cysteine conjugate 16:1, a TWA of 191±47 μp, and with the 2:1 conjugate, a TWA of 280±67 μJ could be attained, while the unmodified polymer had a TWA of 104±21 μJ. It has been shown that the increase in the TWA had an optimum at pH 6.8, yet even at pH 3 positive effects of the thiolated compound occur relative to the starting polymer.

EXAMPLE 2

Assays for the Disintegration of the Polymers According to the Invention

Carboxymethyl cellulose-cysteine conjugate (CMC-cysteine conjugate) and PCP-cysteine conjugate prepared according to the invention were lyophilized and brought into a matrix tablet form. Likewise, tablets comprising the corresponding, non-modified polymers were prepared. The stability of the polymer tablets (30 mg) in 5 ml of 50 mM Tris-HCl-buffered physiological saline solution (TBS), pH 6.8 at 37° C., was analyzed with a disintegration assaying apparatus according to European pharmacopoeia with an oscillation frequency of 0.5 per s.

Figure 2:
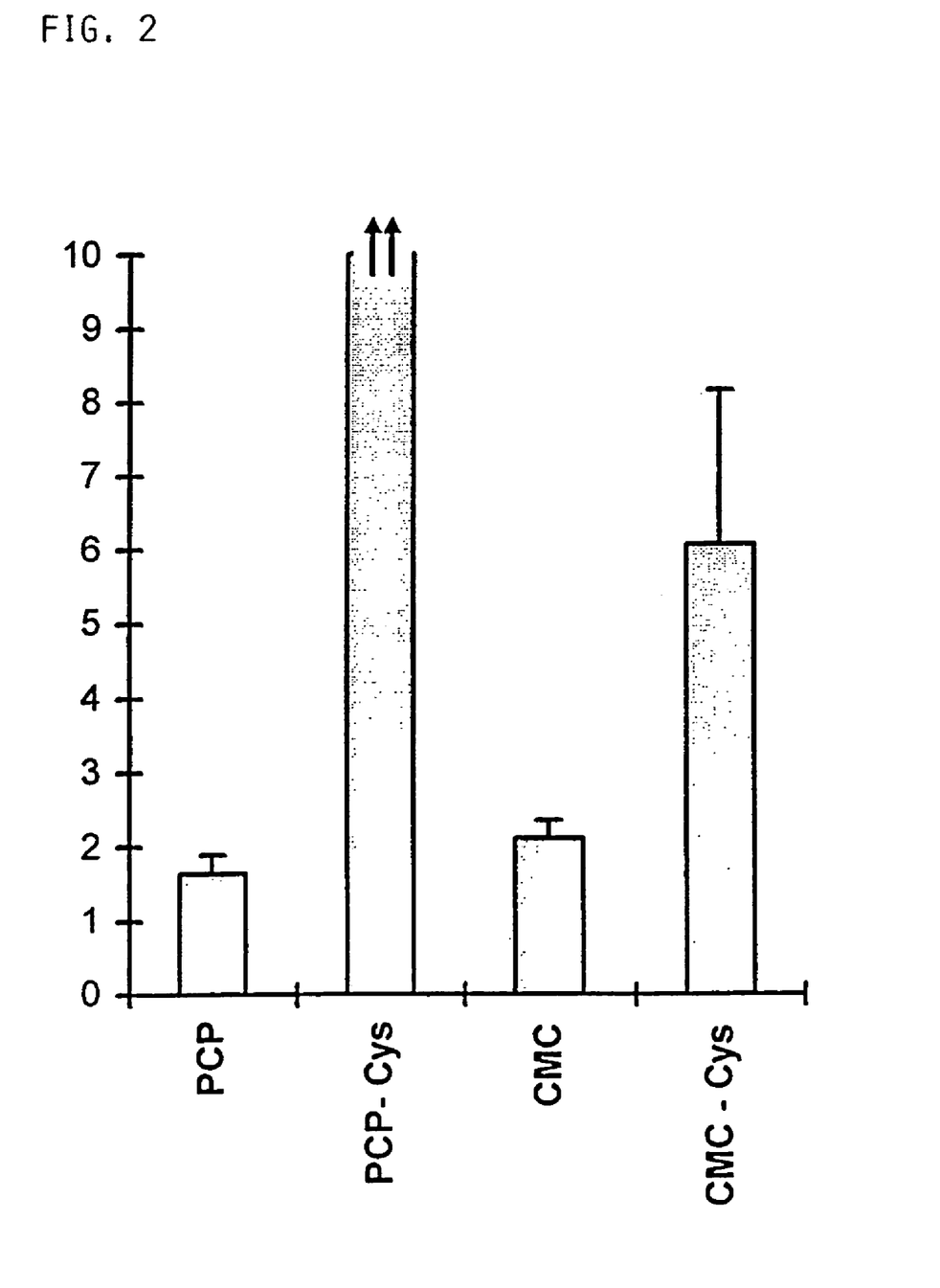
FIG. 2 shows the disintegration of thiolated polymers as compared to the non-modified polymers.

It has been shown that the tablets of thiolated polymers had a substantially higher stability than the non-modified polymers. In the assay, matrix tablets containing the CPC-cysteine conjugate were even stable for several days. The results are illustrated in FIG. 2, the disintegration time being given in hours on the y-axis.

This high stability of the tablets of the polymers according to the invention can be explained by the formation of disulfide bonds in the polymers, by which indirectly also an improved adhesion of the matrix system is made possible, since detachment of the drug from the mucosa by breaking off the bond within the drug can be highly reduced. This improved stability has also substantial practical implications and offers various advantages as compared to the known polymer-carrier systems, primarily as regards the reduction of pre-systemic metabolisms in active polypeptidic substances in the intestines.

EXAMPLE 3

Release Tests

Conjugates prepared according to the invention (CMC-cysteine conjugate and PCP-cysteine conjugate) were hydrated in demineralized water and placed into acetone or 1N NaOH, respectively, thus highly increasing viscosity. After washing with acetone or with methonol, respectively, it was air-dried and powderized.

Tablets were produced consisting of 1 mg of rifampicin as model active substance and 29 mg of the CMC-cysteine conjugate or of the PCP-cysteine conjugate, respectively, as well as the corresponding, non-modified polymers. Subsequently, the in vitro release rate of this active substance delivery system was analyzed by placing the tablets into 25 ml containers containing 10 ml of release medium (50 mM TBS, pH 6.8). The containers were closed and incubated on an oscillating water bath at 37±0.5° C. 600 μl aliquots were taken at one-hour intervals and replaced by equal volumes of release medium. Released rifampicin was photometrically quantitated at 470 nm by means of a calibration curve.

Figure 3A:
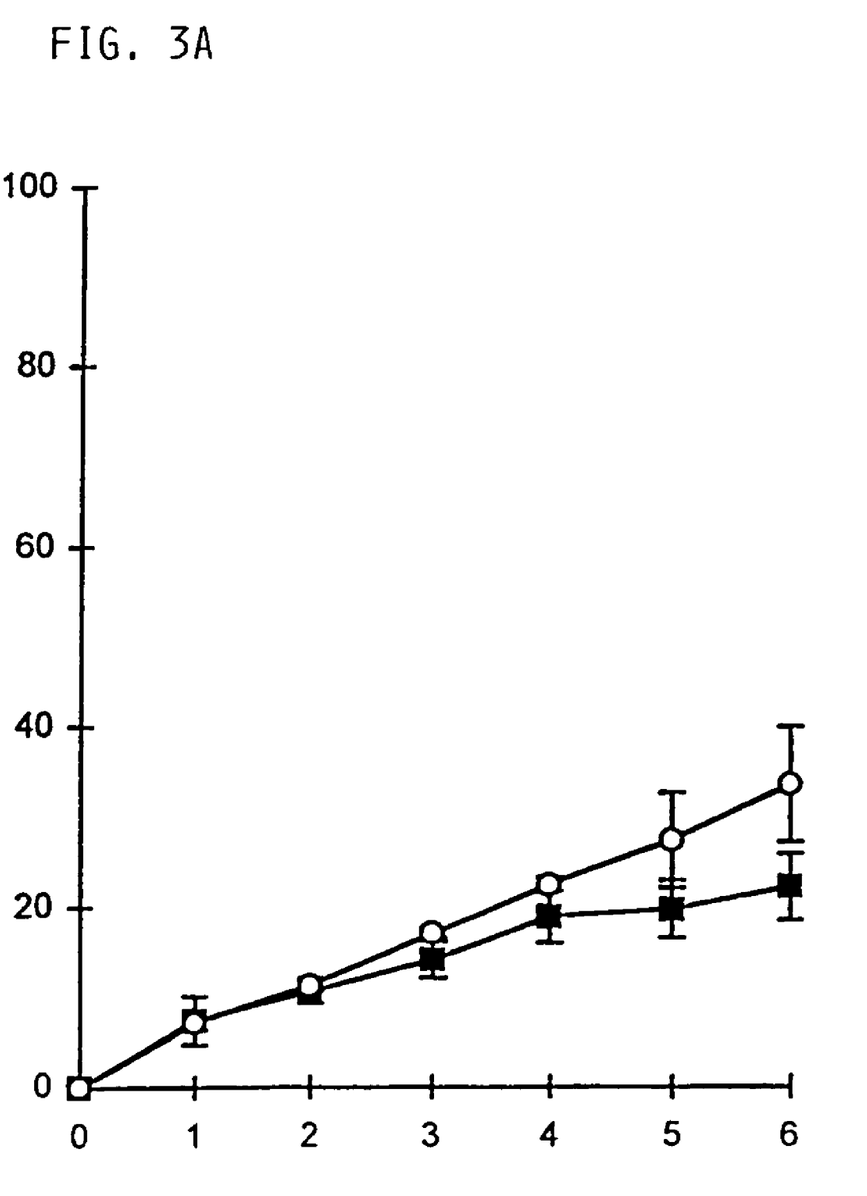
Figure 3B:
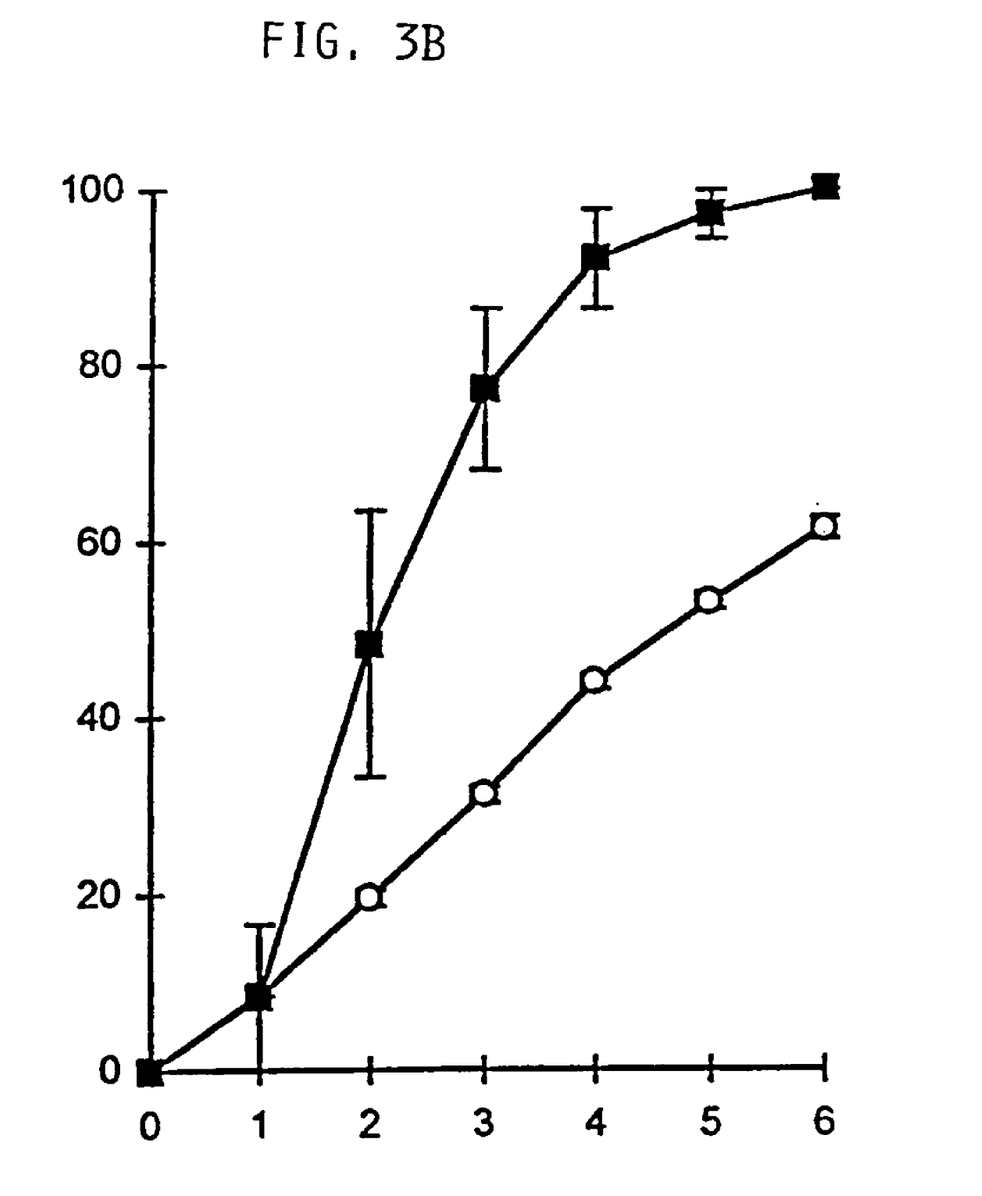

The results are represented in FIG. 3A (for CMC) and FIG. 3B (for PCP), the time being plotted in hours on the x-axis and the percent of released rifampicin on the y-axis.

It has been shown that with the systems according to the invention, a substantially more efficient release is obtained, demonstrating the high potential of the polymers of the invention primarily in view of the disintegration results. A controlled active substance release was achieved for an extended period of time in an efficient manner.

EXAMPLE 4

Activity of the Polymers of the Invention as Permeation Enhancer 2 mg of fluorescein isothiocyanate (FITC) were dissolved in 1 ml of DMSO and added in aliquot volumes of 25 µl to 40 mg of bacitracin (dissolved in 20 ml, 0.1M, $Na_2CO_3$). To stop the coupling reaction after 8 h at 4° C., ammonium chloride was added in a final concentration of 50 mM. The FITC conjugate formed was isolated by gel filtration over Sephadex G15 and lyophilized.

Permeation tests were carried out with this modified peptide at 37° C., using Ussing compartments in pieces of small intestines of guinea pigs. The donor and the acceptor chambers were each filled with 1 ml of a solution containing 250 mM sodium chloride, 2.6 mM magnesium sulfate, 10.0 mM calcium chloride, 40.0 mM glucose and 50 mM sodium hydrogen carbonate (pH 7.2). The bacitracin-FITC conjugate was added to the donor compartment in a final concentration of 0.1% (m/v). Aliquot volumes of 200 µl were taken from the acceptor compartment at certain points of time and replaced by as the same medium. The influence of PCP and thiolated PCP (PCP-Cyst) which had been prepared according to the invention on the permeation behavior of the modified peptide was tested by the addition of 0.5% (m/v) of PCP and 0.5% (m/v) of PCP-Cyst. The amount of permeated bacitracin-FITC conjugate was determined with a fluorimeter. Likewise, the changes in the transepithelial electric resistance were monitored.

It could be demonstrated that bacitracin having a molecular weight of 1422 Da can permeate the intestinal mucosa to a certain degree. A degradation due to digestive enzymes could be excluded because of its enzyme-inhibiting activity. The addition of 0.5% PCP led to a 1.2-fold increase in the transport of the model peptide through the membrane, while the use of the polymers prepared according to the invention allowed for a significantly higher increase (about the 1.5-fold) in the permeation. As comparative experiment, it could be shown that cysteine per se had no influence on permeation, whereby the significant effect of the polymers of the invention has been proven.

Figure 4:
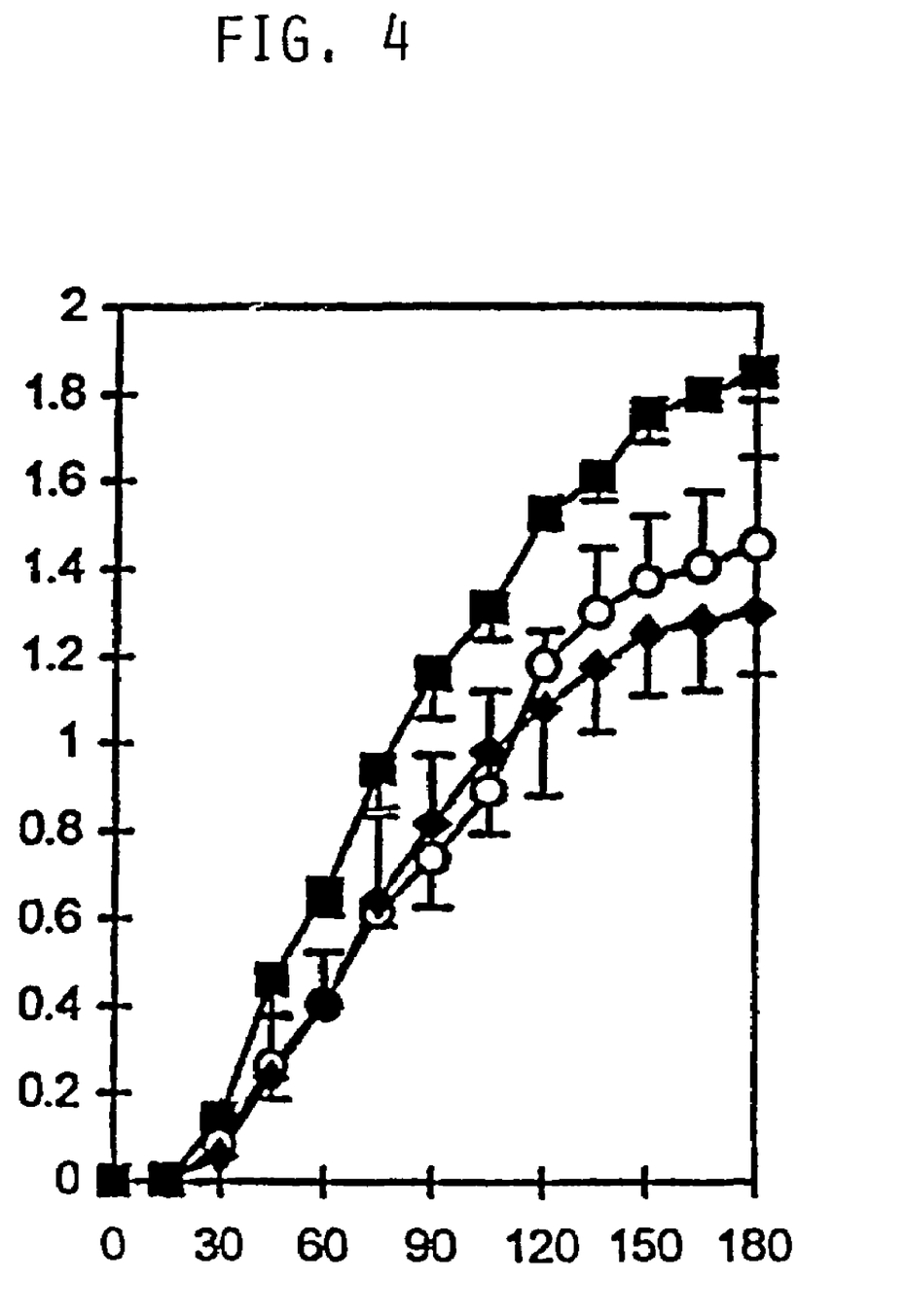
FIG. 4 shows the permeation effect via intestinal mucosa.

The results of this experiment have been illustrated in FIG. 4, with the time in minutes being indicated on the x-axis and the permeation in percent of the entire dose being given on the y-axis (○: PCP ■: PCP-Cyst ♦: control).

EXAMPLE 5

In Vitro-Mucoadhesion Tests

PCP (molecular weight more than 700 kDa) was neutralized with NaOH. The carboxylic acid groups of hydrated, neutralized PCP and hydrated CMC (molecular weight about 1000 kDa) were activated for 45 min by adding 1-ethyl-3-(3-dimethylaminopropyl)-carbodiimide-hydrochloride (EDAC; Sigma) in a final concentration of 50 mM. L-cysteine hydrochloride was added, and the pH of the reaction mixture was adjusted to 4-5. The molar ratio of EDAC to L-cysteine was 50:3.2 and 50:1 for the coupling reactions with PCP and CMC, respectively. The pH of the coupling reaction with CMC was kept constant by adding 1 N HCl. The reaction mixtures were incubated for 3 h at room temperature. The polymer-cysteine conjugates obtained were isolated by dialysis at 10° C. in the dark against 1 mN HCl. Subsequently, the pH of these polymers was adjusted with 1 N NaOH at pH 3, pH 5 or pH 7 and lyophilized. The thiolated polymers obtained had 12.3 mmol (PCP conjugate) and 22.3 µmol (CMC conjugate) thiol groups/g of polymers.

Figure 5:
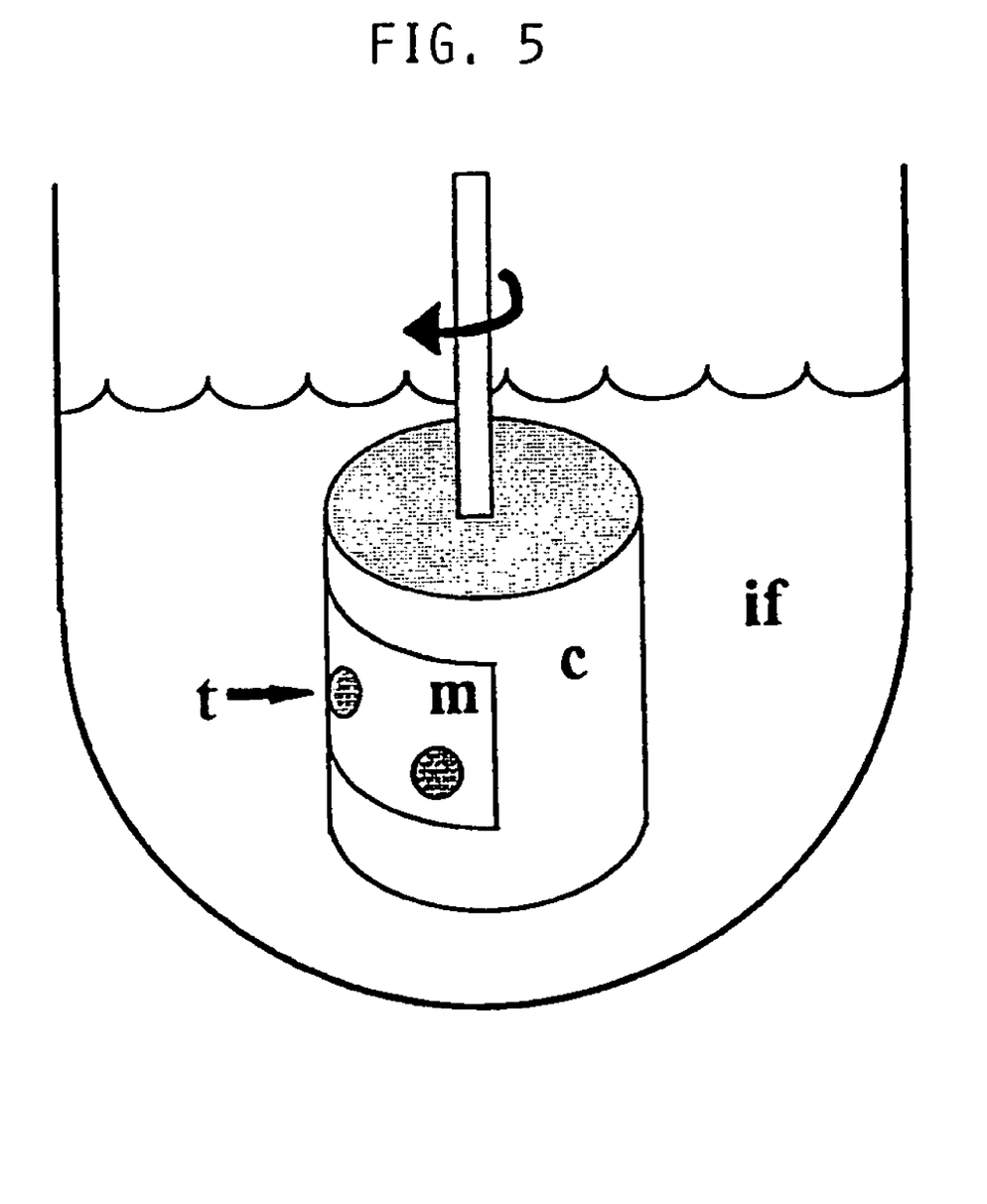
FIG. 5 shows the device for measuring the mucoadhesive properties.

The mucoadhesion tests were carried out with an apparatus according to U.S. pharmacopoiea (cf. FIG. 5): a freshly excised intestinal mucosa from pig was tensioned on a steel cylinder (diameter 4.5 cm, height 5.1 cm, apparatus 4 cylinders, USP XXII). This cylinder was introduced into the dissolution apparatus containing 100 mM TBS, pH 6.8, at 37° C. and moved at 250 rpm. The polymers were pressed to 30 mg tablets with a diameter of 5.0 mm, applied to the mucosa and observed for a period of 10 hours. The results are given in the following table:

| Polymer | pH 3 | pH 5 | pH 7 |
| --- | --- | --- | --- |
| PCP control | 7.5 ± 1.35 dis. | 4.8 ± 1.35 det. | 4.6 ± 1.39 dis. |
| PCP-Cys | 7.55 ± 1.15 dis. | >10 | 2.25 ± 0.87 det. |
| CMC control | 2.0 ± 0.35 det. | 2.5 ± 0.5 dis. | 1.5 ± 0.91 det. |
| CMC-Cys | 3.9 ± 1.02 det. | 3.0 ± 0.35 det. | 1.7 ± 0.57 det. | dis . . . disintegration
det . . . detachment

It has been shown that the polymers according to the invention have clearly improved properties relative to the non-thiolated starting polymers. It has been shown that in the system according to the invention, the cooperation of the properties: capabilities of adhesion to the mucosa, binding mechanism of the inventive polymers to the mucosa, increased cohesion and swelling behavior give rise to an optimum adhesion process allowing for a superior drug supply by optimum adhesion to the mucus layers.

EXAMPLE 6

Enzyme Inhibition Effects

The inhibition effect of PCP-cysteine conjugates and non-modified neutralizing PCP relative to carboxy-peptidase A and carboxy-peptidase B were tested. In doing so, the following was tested in enzyme activity tests described for these enzymes:

0.5 mg of the polymers or of the L-cysteine, respectively, and 0.5 units of carboxy-peptidase A from bovine pancreas were incubated in 400 µl of 25 mM Tris-HCl, pH 6.8, containing 2.9% NaCl for 30 minutes at room temperature. After centrifugation, 300 µl of supernatant were put into 300 µl of 2 mM hippuryl-L-phenyl-alanine, the increase in the absorption being measured at 254 nm at 1 minute intervals.

The polymers (1 mg) and carboxy-peptidase B (0.62 units) from bovine pancreas were incubated in a total volume of 600 µl for 30 minutes at 37° C. After centrifugation, 400 µl of supernatant were put into 400 µl of 2 mM hippuryl-L-arginine, the increase in absorption being measured at 258 nM at 1 minute intervals.

It has been shown that the already present inhibitory effect of PCP relative to carboxy-peptidases A and B could be significantly increased by immobilizing cysteine on the polymer. Since the binding affinity of PCP relative to zinc could be increased by the 1.13-fold by immobilizing cysteine on the polymer (68.7±1.9% zinc are bound to PCP, whereas 97.8±0.5 are bound to the PCP-cysteine), and these exopeptidases are not bound to the polymers, it is clear that the increase in the inhibiting effect is due to the higher zinc affinity of the polymers according to the invention.

EXAMPLE 7

Binding of Cysteine to the Polymer According to the Invention

Figure 6:
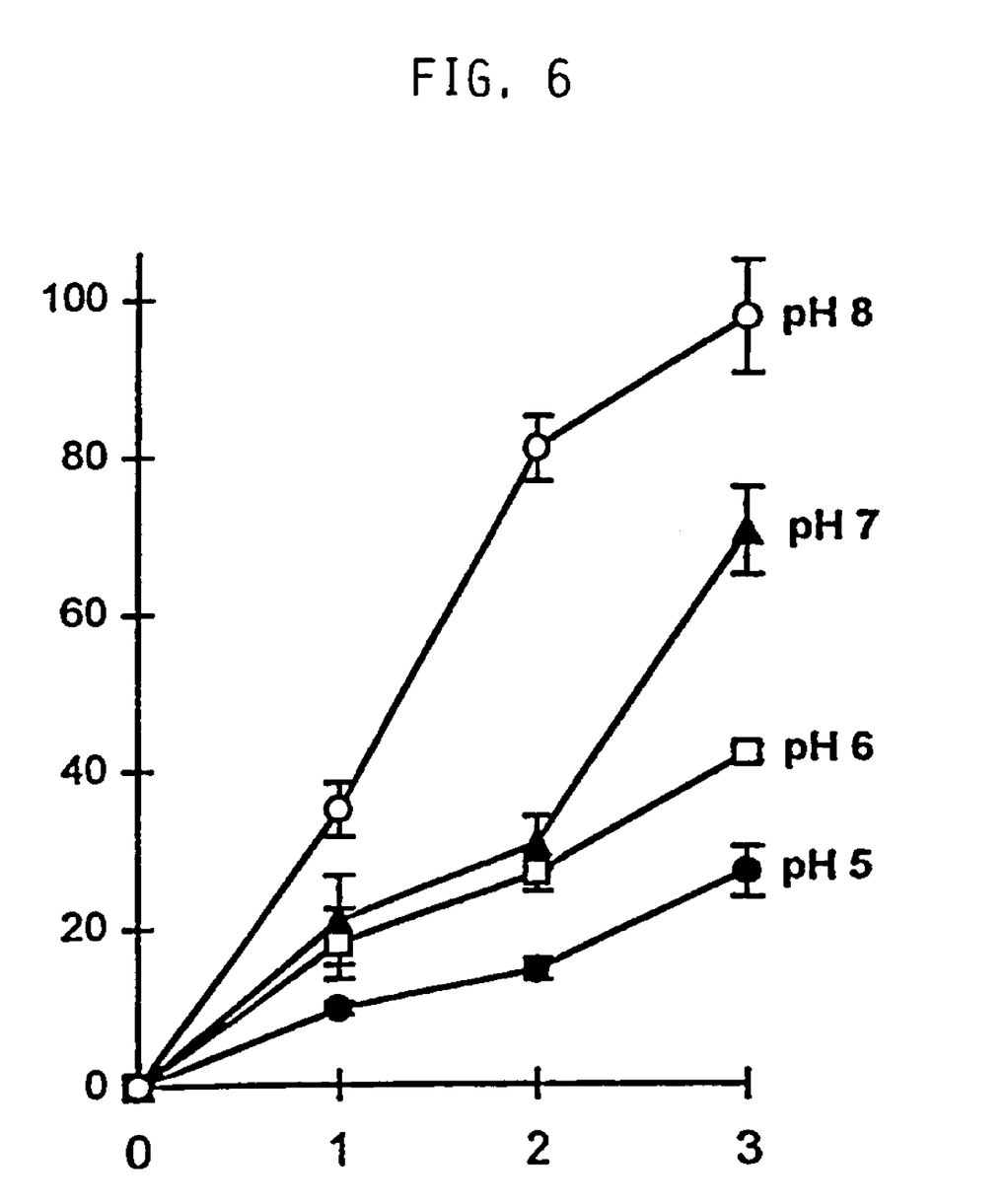
FIG. 6 shows the binding of L-cysteine to thiolated PCP.

In cysteine-binding studies, 0.5% (m/v) of the PCP-cysteine conjugate prepared and 0.1% (m/v) of L-cysteine were incubated at 37° C. at various pH values. The results have been illustrated in FIG. 6: on the x-axis, the time in hours is given, and on the y-axis the bound cysteine is given in % of the theoretical maximum which can be bound to the polymer.

From these binding studies it is clearly apparent that the polymers according to the invention can covalently adhere to cysteine partial structures in biological systems, and thus are also suitable for applications in which an improved adhesion to non-mucous contact areas, such as, i.e., in intradermal, intraarticular and intraocular applications.

The invention claimed is:

1. A thiolated mucoadhesive polymer selected from the group consisting of: a thiolated copolymer of acrylic acid and divinyl glycol, a thiolated polymer of chitosan, a thiolated polymer of sodium carboxymethylcellulose, a thiolated polymer of sodium alginate, a thiolated polymer of sodium hydroxypropylcellulose, a thiolated polymer of hyaluronic acid, and a thiolated polymer of pectin, wherein:
   (a) said thiolated mucoadhesive polymer comprises at least one non-terminal thiol group, and
   (b) said thiolated mucoadhesive polymer exhibits a total work of adhesion (TWA) of more than 120 µJ to intestinal mucosa at a pH of 7.

2. The thiolated mucoadhesive polymer as set forth in claim 1, wherein said thiolated mucoadhesive polymer comprises at least 0.05 µmol of covalently bound thiol groups per gram of polymer.

3. The thiolated mucoadhesive polymer as set forth in claim 2, wherein said thiolated mucoadhesive polymer comprises at least 0.1 µmol of covalently bound thiol groups per gram of polymer.

4. The thiolated mucoadhesive polymer as set forth in claim 1, wherein said thiolated mucoadhesive polymer comprises at least one cysteine group.

5. The thiolated mucoadhesive polymer as set forth in claim 4, wherein said at least one cysteine group is bound to the polymer via an amide bond.

6. The thiolated mucoadhesive polymer as set forth in claim 1, wherein said thiolated mucoadhesive polymer includes at least one monomer having free thiol groups within said thiolated mucoadhesive polymer.

7. The thiolated mucoadhesive polymer as set forth in claim 1, wherein said polymer exhibits a total work of adhesion (TWA) of more than 150 µJ to intestinal mucosa at a pH of 7.

8. The thiolated mucoadhesive polymer as set forth in claim 1, wherein said thiolated mucoadhesive polymer exhibits a total work of adhesion (TWA) increased by at least 30% relative to a mucoadhesive polymer not containing at least one non-terminal thiol group, measured at a pH optimum of the total work of adhesion (TWA) of the thiolated mucoadhesive polymer.

9. The thiolated mucoadhesive polymer as set forth in claim 8, wherein said thiolated mucoadhesive polymer exhibits a total work of adhesion (TWA) increased by at least 50% relative to a mucoadhesive polymer not containing at least one non-terminal thiol group, measured at a pH optimum of the total work of adhesion (TWA) of the thiolated mucoadhesive polymer.

10. The thiolated mucoadhesive polymer as set forth in claim 9, wherein said thiolated mucoadhesive polymer exhibits a total work of adhesion (TWA) increased by at least 100% relative to a mucoadhesive polymer not containing at least one non-terminal thiol group, measured at a pH optimum of the total work of adhesion (TWA) of the thiolated mucoadhesive polymer.

11. A method of preparing a thiolated mucoadhesive polymer of claim 1, said method comprising:
   providing base polymers comprising at least one non-terminal monomer that includes a terminal, functional group I, wherein said terminal, functional group I is free within said polymer,
   providing thiol-containing compounds, wherein said thiol-containing compounds include at least one further functional group II, and wherein said functional groups I and II are together capable of forming a covalent bond, and
   reacting said base polymers with said thiol-containing groups, whereby said functional group I forms a covalent bond with said functional group II to produce a thiolated mucoadhesive polymer of claim 1.

12. A method as set forth in claim 11, further comprising adding coupling reagents when reacting said base polymers with said thiol-containing compounds.

13. The method as set forth in claim 11, wherein said functional group I is a carboxyl group and said functional group II is an amino group.

14. The method as set forth in claim 13, wherein said amino group is a primary amino group.

15. The method as set forth in claim 12, wherein said coupling reagents are carbodiimides, and amide bonds are formed.

16. The method as set forth in claim 11, wherein said thiol-containing compound is a mercapto-compound comprising a primary amino group.

17. The method as set forth in claim 16, wherein said thiol-containing compound is selected from the group consisting of cysteine and a cysteine derivative.

18. The method as set forth in claim 11, wherein said reacting of said base polymers with said thiol-containing groups is performed at a pH of between 4 and 8.

19. The method as set forth in claim 18, wherein said pH is between 5.5 and 6.5.

20. The method as set forth in claim 11, further comprising adjusting said thiolated mucoadhesive polymer to a pH of between 5 and 9.

21. The method as set forth in claim 20, wherein said pH is between 6.5 and 8.5.

22. A method of preparing a thiolated mucoadhesive polymer of claim 1, said method comprising:
   providing base polymers comprising at least one non-terminal monomer that includes a terminal, functional group I, wherein said terminal, functional group I is free within said polymer and wherein said terminal, functional group I is a carboxyl group,
   providing thiol-containing compounds, wherein said thiol-containing compounds include at least one further functional group II, wherein said functional group II is an amino group, and
   reacting said base polymers with said thiol-containing compounds, whereby said functional groups I form a covalent bond with said functional groups II to produce a thiolated mucoadhesive polymer of claim 1.

23. The method as set forth in claim 22, further comprising adding at least one coupling reagent when reacting said base polymers with said thiol-containing compounds.

24. The method as set forth in claim 22, wherein said amino group is a primary amino group.

25. The method as set forth in claim 23, wherein said at least one coupling reagent is a carbodiimide, and amide bonds are formed.

26. The method as set forth in claim 22, wherein said thiol-containing compounds are selected from the group consisting of cysteines and cysteine derivatives.

27. The method as set forth in claim 22, wherein said base polymers are reacted with said thiol-containing compounds at a pH of between 5.5 and 6.5.

28. A thiolated mucoadhesive polymer as set forth in claim 1, wherein said thiolated mucoadhesive polymer is selected from the group consisting of: a thiolated copolymer of acrylic acid and divinyl glycol, a thiolated polymer of chitosan, a thiolated polymer of sodium carboxymethylcellulose, a thiolated polymer of sodium alginate, a thiolated polymer of sodium hydroxypropylcellulose, and a thiolated polymer of pectin.

29. A thiolated mucoadhesive polymer as set forth in claim 1, wherein said thiolated mucoadhesive polymer is a thiolated copolymer of acrylic acid and divinyl glycol.

30. A thiolated mucoadhesive polymer as set forth in claim 1, wherein said thiolated mucoadhesive polymer is a thiolated polymer of chitosan.

31. A thiolated mucoadhesive polymer as set forth in claim 1, wherein said thiolated mucoadhesive polymer is a thiolated polymer of sodium carboxymethylcellulose.

32. A thiolated mucoadhesive polymer as set forth in claim 1, wherein said thiolated mucoadhesive polymer is a thiolated polymer of sodium alginate.

33. A thiolated mucoadhesive polymer as set forth in claim 1, wherein said thiolated mucoadhesive polymer is a thiolated polymer of sodium hydroxypropylcellulose.

34. A thiolated mucoadhesive polymer as set forth in claim 1, wherein said thiolated mucoadhesive polymer is a thiolated polymer of hyaluronic acid.

35. A thiolated mucoadhesive polymer as set forth in claim 1, wherein said thiolated mucoadhesive polymer is a thiolated polymer of pectin.

* * * * *